(12) United States Patent
Novak et al.

(10) Patent No.: US 6,261,285 B1
(45) Date of Patent: Jul. 17, 2001

(54) HIGH-FREQUENCY SURGICAL DEVICE AND OPERATION MONITORING DEVICE FOR A HIGH-FREQUENCY SURGICAL DEVICE

(75) Inventors: Pavel Novak, Schaffhausen; Konrad Kellenberger, Beringen; Felix Daners, Schaffhausen, all of (CH)

(73) Assignee: Storz Endoskop GmbH (CH)

( * ) Notice: Subject to any disclaimer, the term of this patent is extended or adjusted under 35 U.S.C. 154(b) by 0 days.

(21) Appl. No.: 09/043,304

(22) PCT Filed: Sep. 16, 1996

(86) PCT No.: PCT/DE96/01738

§ 371 Date: Mar. 12, 1998

§ 102(e) Date: Mar. 12, 1998

(87) PCT Pub. No.: WO97/09938

PCT Pub. Date: Mar. 20, 1997

(30) Foreign Application Priority Data

Sep. 14, 1995 (DE) .............................................. 195 34 151

(51) Int. Cl.[7] ..................................................... A61B 18/04

(52) U.S. Cl. .............................................................. 606/34
(58) Field of Search ............................. 606/32–34, 37–41

(56) References Cited

U.S. PATENT DOCUMENTS 3,699,967 * 10/1972 Anderson ................................ 606/34
3,946,738 * 3/1976 Newton et al. ......................... 606/34
4,580,562 * 4/1986 Goof et al. ............................. 606/34
5,067,953 * 11/1991 Feucht .................................... 606/34
5,318,563 * 6/1994 Malis et al. ............................ 606/38
5,540,681 * 7/1996 Strul et al. ............................. 606/34

FOREIGN PATENT DOCUMENTS 0 171 967 * 2/1986 (EP) .
0171967A2   2/1986 (EP) .

* cited by examiner

*Primary Examiner*—Michael Peffley
(74) *Attorney, Agent, or Firm*—St. Onge Steward Johnston & Reens LLC

(57) ABSTRACT

A high-frequency surgical device encompassing control electronics that control a power unit which utilizes a high-frequency transformer that is the only galvanic separation between the supply voltage and the patient/user unit.

4 Claims, 2 Drawing Sheets

HIGH-FREQUENCY SURGICAL DEVICE AND OPERATION MONITORING DEVICE FOR A HIGH-FREQUENCY SURGICAL DEVICE

TECHNICAL FIELD

The present invention relates to a high-frequency (HF) surgical device and an operation monitoring device for high-voltage relays which find use in generic type HF-surgical devices and a process for monitoring the operation of high-voltage relays for surgical devices.

STATE OF THE ART

HF-surgical devices of this type are common knowledge. German A-documents 31 51 991, 39 11 416 or 39 42 998 are referred to only by way of example. Moreover, reference is explicitly made to these printed publications for the explanation of all details not described in detail herein or other technical design of HF-surgical devices.

The known HF-surgical device, like other electro-medical devices, have the following problems:

According to IEC 601, electro-medical devices require galvanic separation between the mains-side power supply and the patient/user unit. This galvanic separation occurs in the known generic-type HF-surgical devices by means of a separation transformer which may be either a mains transformer which is connected on the primary side immediately to the mains alternating voltage or is a component of a primary timed combinational mains circuit unit.

High performance high-frequency surgical devices have an output power of 400 W, if need be even more. This means that, depending on the degree of effectivity, approximately 600 W or more power has to be made available at the input side.

A mains transformer designed as a separation transformer, therefore, becomes very voluminous and correspondingly heavy. If a combinational mains circuit unit is employed, the required transformer is small, because usually frequencies between 50 and 100 kHz are worked with, but the cost of the transformer compared to the overall costs cannot be ignored. Moreover, the volume of the device increases.

Another problem with high-frequency surgical devices having more than one outlet respectively several generators is caused by one certain outlet has to be connected to a different generator depending on the mode of operation, by way of illustration cutting or coagulating, bipolar, monopolar etc., is to be employed. In order not to endanger the patient or user, it must be ensured that the high-frequency energy is switched only to the selected outlet.

For switching between the outlets and the generators, a relay matrix having make contacts as operating contacts is employed in order that the outlets are no longer connected to the generator electronics when the device is switched off respectively the switched-off outlets are no longer connected to the generator electronics. Due to, by way of illustration, faulty material, connections can be switched between a switched-off outlet and the generator electronic although the user had switched off this connection. This effect is caused, by way of illustration if the contact of the relay sticks or jams. The errors that the relay coil is interrupted or has a short circuit so that the contact can no longer close is less problematic.

Relays have the characteristic that they need relatively much power in order to pick up contact. This power has to be supplied by the internal supply, usually by an "auxiliary power supply" for the electronic control unit of the high-frequency surgical device. The auxiliary power supply is relatively highly loaded thereby. Therefore, it is desirable to reduce the power intake of the relay.

DESCRIPTION OF THE INVENTION

The object of the present invention is to provide a high-frequency surgical device which meets the pertinent standards for electromagnetic devices such as IEC 601 or VDE 0750 without using a mains separation transformer for galvanic separation of the mains supply and the user unit. Moreover the object of the present invention is to design high-frequency surgical devices more safely and to reduce the power input which auxiliary power supply devices have to fulfill.

The present invention is based on the following understanding: practically every HF surgical device possesses a high-frequency output transformer for power adaptation between the power final stage and the cutting electrode. The transformer is usually operated with a frequency of 0.3 to 1 Mhz.

However, this high-frequency output transformer is not employed in the known HF surgery devices for galvanic separation between the mains supply circuit and the user unit.

An element of the present invention is that it was understood that this HF output transformer can be utilized between the (mains) supply voltage and the patient/user unit. In order to do so, the HF output is designed according to the necessary standards, in particular, regarding the isolation voltage and regarding the air gaps and leakage distances. In particular, a high-frequency transformer that meets the FFIEC 601 respectively VDE 0750 standards can be utilized.

In view of the fact that high-frequency output transformers can be operated with very high frequencies, namely usually 0.3 to 1 mhz, the high-frequency output transformer can be designed small, light and therefore relatively less expensive compared to conventional mains separation transformers or conventional separation transformers in combinational mains circuit units. The invented design not only reduces the costs but also reduces the weight and the overall size of the device.

The operation elements of the control electronics that the user can come into contact with are galvanically separated from the power unit. This galvanic separation, by way of illustration, can occur by means of the construction of the casing, the switches respectively keys employed or by means of transmitters or optoelectronic couplers. This measure permits using a simple universal mains circuit as the internal current supply unit. The measuring signals and also the HF power can be separated by means of greater insulation from the mains.

This embodiment has the advantage that practically no control signals have to be separated between the power unit and the control electronics. However, more attention must be paid to inserting the components in the casing because a comparatively a large leakage distance and air gap is required to the grounded casing.

Preferred is if the control electronics are provided with a separate mains supply circuit.

In order to supply the HF power amplifier with the required power, the "mains supply circuit" is provided with a universal rectifier and a controllable DC/DC converter. The DC/DC converter permits covering the whole mains supply voltage range of 100–240 V alternating voltage. Preferably the DC/DC converter has the property to draw an almost sinus-shaped current from the mains. Due to this, the voltage is less distorted and the RMS current load and therewith the losses in the mains lines are reduced compared to conventional rectifiers.

Furthermore, the present invention is based on the understanding that a sticking relay contact is the most dangerous kind of failure of the control means for the patient respectively for the user. Notably, this kind of failure can result in the energy being simultaneously applied to two outlets. The switching state of the relay is then safe for the persons concerned if the relay is open. Therefore, an element of the present invention is that the function monitoring device checks if the contacts of the relay are being opened.

In order to do so, the function monitoring device for high-voltage relays for surgical devices according to claim 6 requires the following elements:

a control logic for at least one relay,
a controllable voltage supply source,
an inductivity measuring switch, and
drive unit which is provided with at least one relay driver.

The following relay properties are utilized:

1. Relays need a great current in the coil only to switch on. As soon as the contact is closed, a much smaller holding current is needed in order to maintain the contact.

2. The relay coil excites a magnetic circle whose properties change when the relay armature is closed. By way of illustration, due to this the inductivity changes. By closing the relay armature, the connection inductivity increases.

Usually reed relays are employed as relays that can maintain a sufficiently high voltage over the open contact and have a small size. An element of the present invention is that it was understood that a property of reed relays, namely that the relay armature does not move a contact via a mechanical coupling like conventional relays do, but rather that the relay armature itself is the contact, can be advantageously exploited. In this way the connection inductivity already changes when the contact opens or closes. Preferred is therefore to tune the relay driver to the reed relay (claim 7).

Advantageously the function monitoring of the high-voltage relays occurs via the respective control current circuit of the relay to be monitored. Thus no connections are required to the high-frequency outlets For realization of the switch, this has a substantial advantage, because by way of illustration no high-voltage components and no high-frequency components need to be used.

Preferably, an alternating current is superimposed over one outlet of the relay driver. This measure permits easily measuring a change in the inductivity in the relay.

The process for monitoring the function of the high-voltage relay for surgical devices is preferably carried out with the following steps:

application of the smallest possible direct voltage with which all the relays connected to the high frequency outlets pick up,
superimposition of the direct voltage with alternating voltage (AC1)
measurement of the alternating current part and storing this measured value,
application of the largest possible direct voltage with which all the relays connected to the high-frequency outlets close,
superimposition of the direct voltage with the same alternating voltage (AC1)

Measurement of the alternating current part, and
comparison of the measured alternating current part with the stored alternating current part with the addition of a predetermined minimum value.

The measured alternating current part can preferably be stored.

In order to prevent that a relay defect due to a defective function monitoring device cannot be determined, an element of the present invention is that a self-test is conducted.

BRIEF DESCRIPTION OF THE DRAWING

The present invention is made more apparent in the following using preferred embodiments with reference to the drawings, whose figures show the following.

DESCRIPTION OF THE PREFERRED EMBODIMENTS

Figure 1:
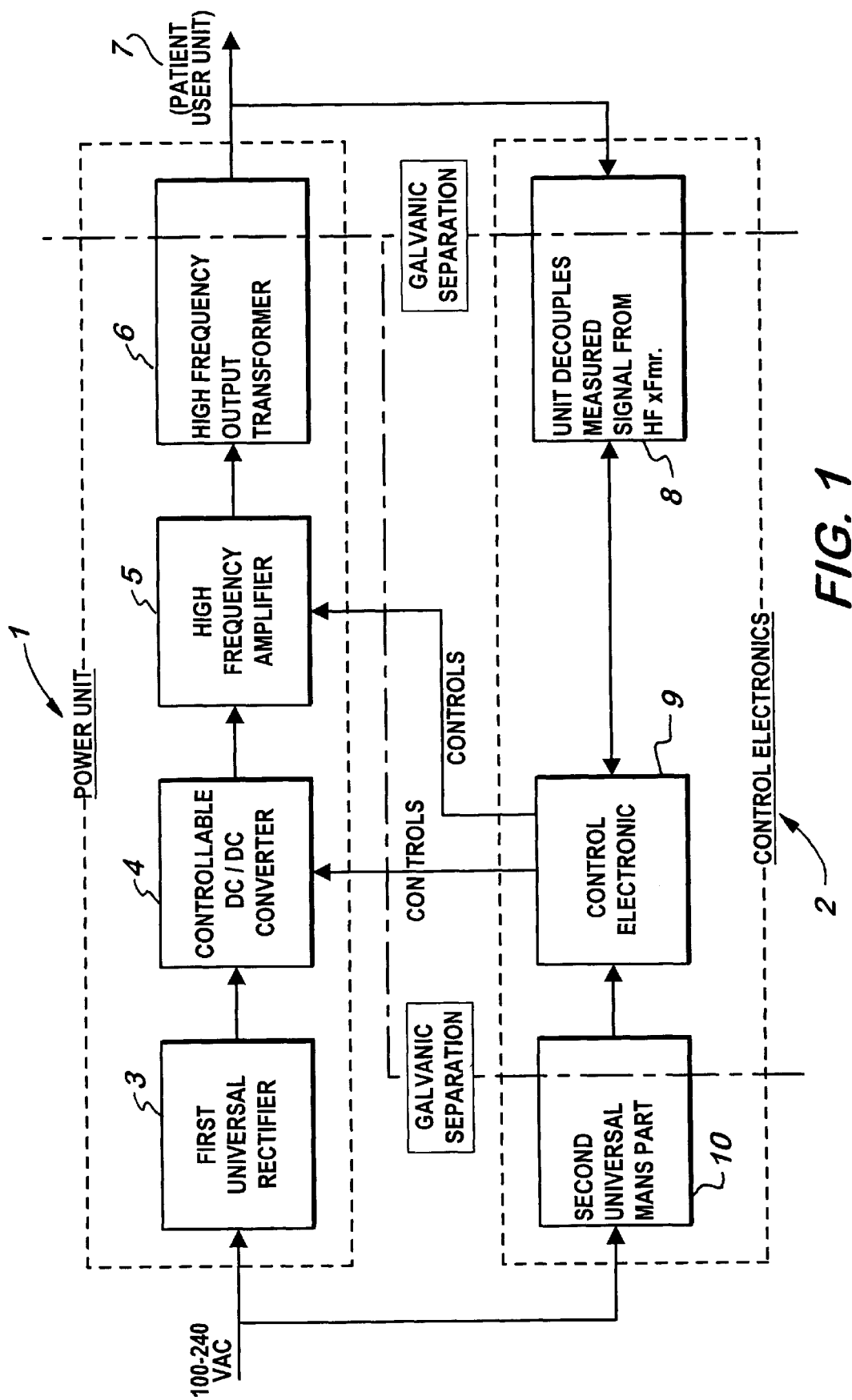
FIG. 1 a block diagram of an invented high-frequency surgical device.

In the block diagram of a high-frequency surgical device shown in FIG. 1, 1 stands for the power unit (blocks in the top row) and 2 stands for the control electronics (blocks in the bottom row) (FIG. 1).

The power unit 1 is provided with a universal rectifier 3 to which the mains alternating voltage, which depending on the national standard can be between 100 and 240V, is applied. The output connection of the universal rectifier 3 is connected to a controllable DC/DC converter 4, which supplies a high-frequency amplifier 5 with power. The output connection of the power amplifier 5 is connected to a high-frequency output transformer 6, which represents the sole galvanic separation between the mains supply voltage and the patient/user unit (arrow 7).

The control electronics 2 is built in a conventional manner. In particular, a unit 8 is provided, by means of which a measured signal from the HF output transformer 6 is decoupled. The output signal of unit 8 is applied to a control electronic 9 which controls both the controllable DC/DC converter 4 and the HF power amplifier 5.

A galvanic separation, which usually fills a 4 kV/8 mm leakage distance, is provided. The galvanic separation may be realized by means of suited switches or, in particular, membrane switches or, by way of illustration, by means of opto-couplers or transmitters.

Furthermore, a second universal mains part 10 can be provided which is designed for low power, by way of illustration 15 W, can be provided for the power supply of the control. electronics. However, the control electronics can also be supplied by an auxiliary power supply respectively voltage which is supplied by the actual mains supply circuit.

A smaller and lighter high-frequency surgical device is yielded by the invented embodiment with little construction input than by the conventional embodiment, in which the galvanic separation between the patient/user unit and the mains supply voltage occurs in the actual mains supply circuit.

Figure 2:
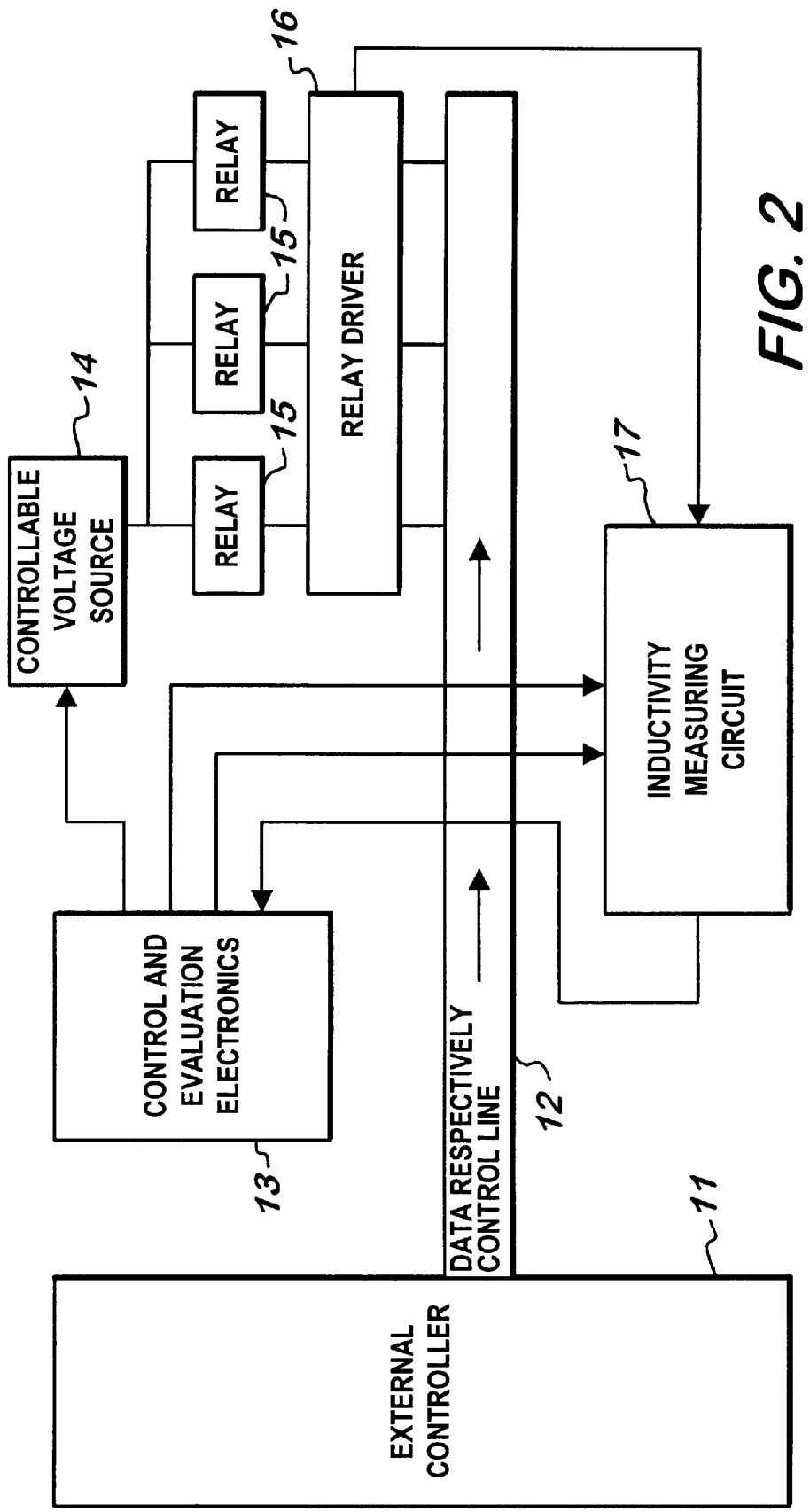
FIG. 2 a block diagram of an invented function monitoring device.

The invented measuring principle for monitoring the function of high-voltage relays for surgical devices is to be shown in the following using FIG. 2: By way of illustration, the point of departure is a surgical device with three outlets. In this embodiment the device has three relays 15.

In order to determine whether the armature of relay 15 moves in a magnetic circle and the contact thus opens respectively closes, the change in inductivity of the relay coil is measured. In order to determine the inductivity, the direct voltage, which is required to build up the magnetic circle and to close the contact, is superimposed with a small alternating voltage. The current generated by the alternating voltage is used as a value for determining the inductivity, with the absolute values being of no interest. Only the change in inductivity is observed. This permits, by way of illustration, using relays from various manufacturers. Moreover, the circuit no longer requires expensive components or complicated balancing. It is to be noted that this principle works readily only with reed relays.

The change in inductivity is determined in two phases: In this embodiment, the procedure takes approximately 18 ms.

1. Phase: The smallest possible direct voltage, with which all the relays pick up, in this case 12V, is applied to the relay. This voltage is superimposed with a square wave voltage of 0.5V with 650 Hz. In order to measure the current, the drop in voltage is measured via a 1 ohm precision resistor. The voltage resulting over the resistor is decoupled with a capacitor in order to evaluate only the alternating voltage part. This AC signal is now amplified and rectified with a peak value rectifier; this voltage is stored with a holding amplifier (sample and hold).

2. Phase: The largest possible direct voltage, with which all the relays close, in this case 2V, is applied to the relay. The same voltage is superimposed as in the first phase. A new voltage now sets in at the peak value rectifier, because the inductivity of the open contact is smaller. This voltage is compared with the stored voltage by means of a comparator. If the new value increases by a predetermined minimum value, the contact has opened correctly. If the voltage changes too little, it has to be assumed that the contact is sticking or that another component is defect.

In this embodiment, the inductivity measuring circuit 17 contains a high-pass filter, an amplifier, a peak value rectifier respectively a peak detector, a holding amplifier and a comparator. The alternating current is measured via a shunt resistor through which a current flows coming from the selected relay in the relays driver 16.

By restricting the DC voltage range to a minimum pick up voltage and a maximum drop-out voltage of the relay, measurement accuracy is improved; simultaneously both these relay parameters are monitored.

Furthermore, it must be taken into account that the relay holding voltage becomes substantially smaller when a contact is interrupted, because the spring force for opening the contact is missing.

The invented circuit can therefore be utilized in such a manner that each relay is tested upon switching off. Therefore, the contact is open after testing and represents the safest state. In this way it is achieved that at no time is HF energy applied to an outlet that was not switched on.

The circuit can, of course, also analogously be utilized to test the relays when switching on.

The circuit is set up in such a manner that only one control and evaluation electronics 13 is required for any number of relays 15. The activation of the relay is assumed by an external controller 11.

Particular attention must be paid to the fact that the evaluation of the relay state is determined solely via the control current circuit and therefore requires no connection to the HF outlets. In this case, the control and evaluation circuit has four circuit parts:

micro-controller
controllable voltage source
inductivity measuring circuit relay driver.

The external controller 11 has an input connection and two output connections so that three data lines are available for communication.

Via one connection, the external controller informs the trigger circuit whether a relay has to be activated or whether a relay has to be tested. The purpose of the other two connections is synchronization and feedback of the test results. Via the data respectively control line 12, the relay driver 16 is informed which relays should be switched on.

The circuit can trigger any number of relays. In this embodiment, however, only one can be tested at one time. In this embodiment, the external controller is responsible for correctly interpreting the data from the evaluation circuit and selecting the desired relays.

In addition, the trigger circuit is set up in such a manner that every first error is detected in the trigger circuit by means of a self-test and transmitted to the controller.

In order to activate a relay, the external controller triggers the relay driver and the trigger circuit is informed that one or more relays are to be switched on. On the basis of this signal (log.1), the power supply voltage of the relays is raised by the controllable voltage source 14 for 5 ms so that the relays can pick up safely. Subsequently, the power supply voltage is reduced so that only a little more than the holding current flows through each relay coil. The reduction of the power supply voltage occurs, by way of illustration by clocking the direct voltage. The pulse/pause ratio reduces the power. The advantage of this triggering is that there are only small losses in the voltage source and that the overall current consumption drops.

The same signal (log. 0) informs the trigger circuit that a relay is to be tested. Thus, the test mode is always run through upon switching off this signal. It is the responsibility of the external controller to set the right relay and ensure correct, timed triggering.

An error or defect in the trigger circuit could prevent detection of a relay defect. Therefore, it is necessary that a circuit self-test is conducted. This self-test does not require additionally components and is conducted autonomically. It is not activated from the outside and not detected If an error is detected, the outlets of the microcontroller are closed. In this manner, the external controller can detect a circuit defect.

What is claimed is:

1. A high-frequency surgical device encompassing: a power supply unit, which is provided with a high-frequency transformer for transforming a supply voltage to an output voltage; control electronics for controlling the output of the power amplifier to the high-frequency transformer; and
   a patient/use unit connected to the output of the high-frequency transformer, said high-frequency transformer being the sole galvanic separation between the supply voltage and the patient/use unit.

2. A device according to claim 1, wherein said control electronics are galvanically separated from said power unit.

3. A device according to claim 1 wherein said control electronics include an element galvanically separating it from the power unit and selected from the group consisting of opto-coupler, transmitters, utilized switches and keys.

4. A device according to claim 1 wherein said control electronics are provided with a separate supply circuit.

* * * * *